(12) United States Patent
Deshpande et al.

(10) Patent No.: US 8,567,608 B2
(45) Date of Patent: Oct. 29, 2013

(54) METHOD AND APPARATUS FOR SORTING PARTICLES

(75) Inventors: Manish Deshpande, Canton, MA (US); John Gilbert, Brookline, MA (US)

(73) Assignee: Cytonome/ST, LLC, Boston, MA (US)

(*) Notice: Subject to any disclaimer, the term of this patent is extended or adjusted under 35 U.S.C. 154(b) by 0 days.

(21) Appl. No.: 12/499,254

(22) Filed: Jul. 8, 2009

(65) Prior Publication Data

US 2010/0032350 A1 Feb. 11, 2010

Related U.S. Application Data

(60) Continuation of application No. 11/101,038, filed on Apr. 6, 2005, now Pat. No. 7,569,788, which is a division of application No. 10/329,008, filed on Dec. 23, 2002, now Pat. No. 6,976,590, which is a continuation-in-part of application No. 10/179,488, filed on Jun. 24, 2002, now Pat. No. 6,808,075.

(60) Provisional application No. 60/411,058, filed on Sep. 16, 2002, provisional application No. 60/373,256, filed on Apr. 17, 2002.

(51) Int. Cl.
*B07C 5/00* (2006.01)

(52) U.S. Cl.
USPC .......................................... 209/552; 209/906

(58) Field of Classification Search
USPC .................... 209/210, 552, 644, 906, 932; 422/502–504
See application file for complete search history.

(56) References Cited

U.S. PATENT DOCUMENTS

| 3,289,687 | A | | 12/1966 | Dunaway |
| 3,506,654 | A | | 4/1970 | Fried |
| 3,508,654 | A | | 4/1970 | Glaettli |
| 3,508,655 | A | | 4/1970 | Kamentsky |
| 3,560,754 | A | | 2/1971 | Kamentsky |
| 3,791,517 | A | * | 2/1974 | Friedman ...................... 209/579 |
| 3,827,555 | A | | 8/1974 | Kamentsky et al. |
| 3,984,307 | A | | 10/1976 | Kamentsky et al. |

(Continued)

FOREIGN PATENT DOCUMENTS

| EP | 0177718 A | 4/1986 |
| EP | A 0 177 718 A | 4/1986 |

(Continued)

OTHER PUBLICATIONS

Chinese Office Action for Application No. 03814212.0, dated Feb. 20, 2009.

(Continued)

*Primary Examiner* — Joseph C Rodriguez
(74) *Attorney, Agent, or Firm* — McCarter & English, LLP; David R. Burns

(57) ABSTRACT

A method and apparatus for sorting particles moving through a closed channel system of capillary size comprises a bubble valve for selectively generating a pressure pulse to separate a particle having a predetermined characteristic from a stream of particles. The particle sorting system may further include a buffer for absorbing the pressure pulse. The particle sorting system may include a plurality of closely coupled sorting modules which are combined to further increase the sorting rate. The particle sorting system may comprise a multi-stage sorting device for serially sorting streams of particles, in order to decrease the error rate.

13 Claims, 8 Drawing Sheets

(56) References Cited

U.S. PATENT DOCUMENTS

| | | | |
|---|---|---|---|
| 3,984,621 A | 10/1976 | Propst | |
| 4,147,621 A | 4/1979 | Giddings | |
| 4,175,662 A * | 11/1979 | Zold | 209/552 |
| 4,318,483 A | 3/1982 | Lombardo et al. | |
| 4,361,400 A | 11/1982 | Gray et al. | |
| 4,365,719 A | 12/1982 | Kelly et al. | |
| 4,426,451 A | 1/1984 | Columbus | |
| 4,526,276 A | 7/1985 | Shoor et al. | |
| 4,554,427 A | 11/1985 | Flick et al. | |
| 4,572,664 A | 2/1986 | Hanson et al. | |
| 4,676,274 A | 6/1987 | Brown | |
| 4,756,427 A | 7/1988 | Gohde et al. | |
| 4,908,112 A | 3/1990 | Pace | |
| 4,936,465 A | 6/1990 | Zold | |
| 4,939,081 A | 7/1990 | Figdor et al. | |
| 5,030,002 A | 7/1991 | North, Jr. | |
| 5,065,978 A | 11/1991 | Albarda et al. | |
| 5,092,972 A | 3/1992 | Ghowsi | |
| 5,101,978 A | 4/1992 | Marcus | |
| 5,193,688 A * | 3/1993 | Giddings | 209/155 |
| 5,275,787 A | 1/1994 | Yuguchi et al. | |
| 5,395,588 A | 3/1995 | North, Jr. et al. | |
| 5,637,496 A | 6/1997 | Thaler et al. | |
| 5,777,649 A | 7/1998 | Otsuka et al. | |
| 5,783,446 A | 7/1998 | Saul et al. | |
| 5,789,045 A | 8/1998 | Wapner et al. | |
| 5,795,727 A | 8/1998 | Bierre et al. | |
| 5,837,200 A * | 11/1998 | Diessel et al. | 422/73 |
| 5,885,470 A | 3/1999 | Parce et al. | |
| 5,932,100 A * | 8/1999 | Yager et al. | 210/634 |
| 5,976,336 A | 11/1999 | Dubrow et al. | |
| 5,979,664 A | 11/1999 | Brodeur | |
| 5,998,212 A | 12/1999 | Corio et al. | |
| 6,046,056 A * | 4/2000 | Parce et al. | 506/39 |
| 6,048,734 A | 4/2000 | Burns et al. | |
| 6,057,111 A | 5/2000 | Deiss et al. | |
| 6,062,681 A | 5/2000 | Field et al. | |
| 6,102,530 A | 8/2000 | Kim et al. | |
| 6,120,666 A | 9/2000 | Jacobson et al. | |
| 6,145,247 A | 11/2000 | McKinnis | |
| 6,152,181 A | 11/2000 | Wapner et al. | |
| 6,196,525 B1 | 3/2001 | Ganan-Calvo | |
| 6,214,556 B1 | 4/2001 | Olek et al. | |
| 6,221,654 B1 * | 4/2001 | Quake et al. | 435/287.3 |
| 6,273,553 B1 | 8/2001 | Kim et al. | |
| 6,280,967 B1 | 8/2001 | Ransom et al. | |
| 6,360,775 B1 | 3/2002 | Barth et al. | |
| 6,432,630 B1 | 8/2002 | Blankenstein | |
| 6,454,862 B1 | 9/2002 | Yoshida et al. | |
| 6,455,280 B1 | 9/2002 | Edwards et al. | |
| 6,482,652 B2 | 11/2002 | Furlong et al. | |
| 6,524,790 B1 | 2/2003 | Kopf-Sill et al. | |
| 6,540,895 B1 | 4/2003 | Spence et al. | |
| 6,561,224 B1 | 5/2003 | Cho | |
| 6,592,821 B1 | 7/2003 | Wada et al. | |
| 6,597,438 B1 | 7/2003 | Cabuz et al. | |
| 6,657,730 B2 | 12/2003 | Pfau et al. | |
| 6,803,194 B1 | 10/2004 | Keck et al. | |
| 6,808,075 B2 | 10/2004 | Bohm et al. | |
| 6,821,484 B1 | 11/2004 | Gregersen | |
| 6,877,528 B2 | 4/2005 | Gilbert et al. | |
| 6,976,590 B2 | 12/2005 | Deshpande et al. | |
| 7,075,652 B1 | 7/2006 | Sarvazyan et al. | |
| 7,104,405 B2 | 9/2006 | Bohm et al. | |
| 7,157,274 B2 | 1/2007 | Bohm et al. | |
| 7,157,275 B2 | 1/2007 | Guarino | |
| 7,220,594 B2 | 5/2007 | Foster et al. | |
| 7,258,774 B2 | 8/2007 | Chou et al. | |
| 7,389,879 B2 * | 6/2008 | Tyvoll et al. | 209/3.1 |
| 7,452,725 B2 * | 11/2008 | Leary et al. | 436/63 |
| 7,497,334 B2 | 3/2009 | Tyvoll | |
| 7,569,788 B2 | 8/2009 | Deshpande et al. | |
| 7,584,857 B2 | 9/2009 | Bohm et al. | |
| 7,820,427 B2 * | 10/2010 | Unger et al. | 435/286.5 |
| 7,963,399 B2 | 6/2011 | Bohm et al. | |
| 2002/0005354 A1 | 1/2002 | Spence | |
| 2002/0058332 A1 | 5/2002 | Quake et al. | |
| 2002/0093641 A1 | 7/2002 | Ortyn et al. | |
| 2003/0027225 A1 | 2/2003 | Wada et al. | |
| 2004/0180426 A1 | 9/2004 | Maher | |
| 2006/0177348 A1 | 8/2006 | Yasuda | |
| 2007/0065808 A1 | 3/2007 | Bohm et al. | |
| 2010/0032350 A1 | 2/2010 | Deshpande et al. | |
| 2010/0133151 A1 | 6/2010 | Bohm et al. | |
| 2011/0005978 A1 | 1/2011 | Bohm et al. | |
| 2012/0006727 A1 | 1/2012 | Bohm et al. | |
| 2012/0012508 A1 | 1/2012 | Deshpande et al. | |

FOREIGN PATENT DOCUMENTS

| | | |
|---|---|---|
| EP | 0177718 | 12/1989 |
| EP | 0745682 A | 12/1996 |
| EP | A 0 745 682 A | 12/1996 |
| EP | 0745682 | 11/2001 |
| GB | 2 229 649 | 10/1990 |
| GB | 2229649 | 10/1990 |
| JP | A S49-46274 | 5/1974 |
| JP | S49-046274 | 5/1974 |
| JP | A S61-137062 | 6/1986 |
| JP | S61-137062 | 6/1986 |
| JP | S63-259466 | 10/1988 |
| JP | A H01-170853 | 7/1989 |
| JP | H01-170853 | 7/1989 |
| JP | H03-043070 | 2/1991 |
| JP | H05-506180 | 9/1993 |
| JP | H06-507241 | 8/1994 |
| JP | A H08-332074 | 12/1996 |
| JP | H08-332074 | 12/1996 |
| JP | H09-141124 | 6/1997 |
| JP | H11-508182 | 7/1999 |
| JP | 2001-521755 | 11/2001 |
| JP | 2002-503334 | 1/2002 |
| JP | A 2002-503334 | 1/2002 |
| JP | 2004-505272 | 2/2004 |
| JP | A 2004-505272 | 2/2004 |
| WO | WO-91/14505 | 10/1991 |
| WO | WO 91/14505 | 10/1991 |
| WO | WO 91/15750 | 10/1991 |
| WO | WO-91/15750 | 10/1991 |
| WO | WO 9115750 | 10/1991 |
| WO | WO 98/07069 | 3/1998 |
| WO | WO 98/10267 | 3/1998 |
| WO | WO-98/10267 A1 | 3/1998 |
| WO | WO-98/52691 | 11/1998 |
| WO | WO 98/52691 | 11/1998 |
| WO | WO 99/23471 | 5/1999 |
| WO | WO-99/23471 | 5/1999 |
| WO | WO 00/70080 | 11/2000 |
| WO | WO-00/70080 A1 | 11/2000 |
| WO | WO 02/10713 | 2/2002 |
| WO | WO 02/010713 | 2/2002 |
| WO | WO 02/44689 | 6/2002 |
| WO | WO 02/044689 | 6/2002 |

OTHER PUBLICATIONS

Australian Office Action for Application No. 2003228630, dated Feb. 11, 2008.

Chinese Office Action for Application No. 03825178.7, dated Jun. 27, 2008.

Chinese Office Action for Application No. 03825178.7 dated Sep. 18, 2009.

Japanese Office Action for Application No. 2004-536583 dated Sep. 18, 2009.

Supplementary European Search Report for Application No. 03752432.9 dated Aug. 21, 2009.

Supplementary European Search Report for Application No. 03726391.0 dated Oct. 6, 2009.

Australian Examiner's Report for Application No. 2003270722, dated Aug. 26, 2009.

Office Action in Japanese Application No. 2007-315437, dated May 11, 2011.

(56) References Cited

OTHER PUBLICATIONS

Office Action issued in Canadian Patent Application No. 2,482,869 dated Dec. 17, 2010.
Examination Report issued in Indian Patent Application No. 1587/KOLNP/2004 dated Jul. 15, 2010.
Office Action issued in U.S. Appl. No. 12/537,802 dated Jun. 18, 2010.
Notice of Reasons for Rejection issued in Japanese Patent Application No. 2007-315437 dated May 12, 2010.
Office Action issued in U.S. Appl. No. 11/603,444, dated Dec. 23, 2009.
Australian Written Opinion and Search Report issued for Singapore Application 200701943-3 dated Oct. 23, 2009.
Communication Pursuant to Article 94(3) EPC issued in European Patent Application No. 03 726 391.0-2204 dated Apr. 12, 2010.
Office Action issued in Canadian Patent Application No. 2,482,869 dated Feb. 16, 2010.
Examiner's Report issued in Australian Patent Application No. 2010200179 dated Mar. 22, 2011.
Office Action issued in Chinese Application No. 03814212.0, dated Apr. 25, 2008.
International Preliminary Examination Report issued in International Application No. PCT/US03/29198, dated Feb. 21, 2006.
International Search Report issued in International Application No. PCT/US03/29198, dated Jun. 10, 2005.
International Preliminary Examination Report issued in International Application No. PCT/US03/12368, dated Aug. 25, 2004.
International Search Report issued in International Application No. PCT/US03/12368, dated Aug. 21, 2003.
International Preliminary Examination Report issued in International Application No. PCT/US03/12359, dated Nov. 12, 2003.
International Search Report issued in International Application No. PCT/US03/12359, dated Jun. 28, 2003.
Second Office Action issued in Chinese Application No. 03825178.7, dated Mar. 20, 2009.
Office Action issued in Israeli Application No. 167266, dated Sep. 28, 2010.
Office Action issued in Japanese Application No. 2003-585899, dated Jan. 11, 2008.
Office Action issued in Japanese Application No. 2003-585899, dated Jun. 6, 2007.
Examination Report issued in Canadian Patent Application No. 2,482,869, dated Sep. 13, 2011.

* cited by examiner

METHOD AND APPARATUS FOR SORTING PARTICLES

RELATED APPLICATIONS

The present application is a continuation of Ser. No. 11/101,038, filed Apr. 6, 2005, which, in turn, is a divisional of 10/329,008, filed Dec. 23, 2002, now U.S. Pat. No. 6,976,540, which claims priority to U.S. Provisional Patent Application Ser. No. 60/411,058, filed Sep. 16, 2002, and is a continuation-in-part of U.S. patent application Ser. No. 10/179,488, filed Jun. 24, 2002, now U.S. Pat. No. 6,808,075, which claims priority to U.S. Provisional Patent Application No. 60/373,256, filed Apr. 17, 2002, the contents of each application and patent are herein incorporated by reference in their entirety.

FIELD OF THE INVENTION

The invention relates to a method and apparatus for the sorting of particles in a suspension, where the input flow path of a sorting module can be split into several output channels. More particular, the invention relates to a particle sorting system in which a plurality of sorting modules are interconnected as to yield an increased particle throughput.

BACKGROUND OF THE INVENTION

In the fields of biotechnology, and especially cytology and drug screening, there is a need for high throughput sorting of particles. Examples of particles that require sorting are various types of cells, such as blood platelets, white blood cells, tumorous cells, embryonic cells and the like. These particles are especially of interest in the field of cytology. Other particles are (macro) molecular species such as proteins, enzymes and poly-nucleotides. This family of particles is of particular interest in the field of drug screening during the development of new drugs.

Methods and apparatus for particle sorting are known, and the majority described in the prior art work in the condition where the particles are suspended in a liquid flowing through a channel network having at least a branch point downstream and are operated according to the detect-decide-deflect principle. The moving particle is first analyzed for a specific characteristic, such as optical absorption, fluorescent intensity, size etc. Depending on the outcome of this detection phase, it is decided how the particle will be handled further downstream. The outcome of the decision is then applied to deflect the direction of specific particle towards a predetermined branch of the channel network.

Of importance is the throughput of the sorting apparatus, i.e. how many particles can be sorted per unit of time. Typical sorting rates for sorters employing flows of particle suspension in closed channels are in the range from a few hundred particles per second to thousands of particles per second, for a single sorting unit.

An example of a sorting device is described in U.S. Pat. No. 4,175,662, the contents of which are herein incorporated by reference (hereinafter referred to as the '662 patent). In the '662 patent, a flow of particles, cells in this case, flows through the center of a straight channel, which branches into two perpendicular channels at a branching point downstream (T-branch). The entering particles are surrounded by a sheath of compatible liquid, keeping the particles confined to the center of the channel. In normal conditions, the flow ratio through the two branches is adjusted so that the particles automatically flow through one of the branches. In a section of the channel a characteristic of the particles is determined using a detector, which can be an optical system (detection phase). The detector generates a signal when the detector detects a particle possessing a predetermined characteristic in the decision phase. Once a particle is detected, a deflector is activated for deflecting the particle in a deflection phase. In this case, the deflector comprises an electrode pair, positioned in the branch of the channel where the particles normally flow through in the inactivated state of the deflector. By the application of current pulses, the aqueous liquid is electrolysed, yielding a gas bubble evolving between the electrode pair. As the gas bubble increases in size, the flow rate through this branch is reduced during the evolving phase. After the current pulse is applied, the bubble growth stops and the gas bubble is carried along with the flow. As a result, the flow through the specific branch is momentarily reduced and the particle of interest changes paths and flows down the other branch.

The device of the '662 patent is effective for sorting particles. However one serious drawback is that gas bubbles are created which potentially can accumulate at certain points of the fluidic network. This bubble generation can clog the flow channels, yielding erroneous sorting. Another drawback is that the generated gasses (mostly oxygen and hydrogen) and ionic species (mostly $OH^-$ and $H^+$) influence the particles flowing through the branch with the electrode pair. In addition, cells and delicate proteins such as enzymes are very fragile and can be destroyed by the fouling constituents co-generated with the gas bubble. Another drawback is the complexity of the overall sorting apparatus. In particular, the micro electrode construction is very complex to mount and assemble in the small channels of the system. As a result, the cost of a sorting unit is relatively large.

Another example of a particle sorting system of the prior art is disclosed in U.S. Pat. No. 3,984,307, the contents of which are herein incorporated by reference (hereinafter the '307 patent). In the '307 patent, the particles are flowing, confined by a flowing sheath liquid, through the center of a channel. After passing a detector section, the channel branches into two channels forming an acute angle therebetween (e.g., Y-branch). Just before the branching point, an electrically activated transducer is located in the channel for deflecting a specific particle having an appropriate, predetermined characteristic. The transducer described is a piezo actuator or ultrasonic transducer, yielding upon electrical activation a pressure wave in the channel. The generated pressure wave momentarily disturbs the flow in one branch thus deflecting the particle of interest into the other branch.

In the device of the '307 patent, as in the previous discussed device, the deflector is incorporated within the channel system, resulting in relatively large construction costs. Another drawback of this device is the deflector principle used. The generated pressure waves are not confined to the branching point, but rather propagate upstream into the detector section, as well as down both branches. This influences the overall flow through the channel. This is particularly a drawback if sorters of this type are connected either in series or in parallel, as is typically done to construct a high throughput sorting system. Pressure waves generated in one sorter can then influence the flows and deflection of particles in neighboring sorter units.

Another sorter is described in U.S. Pat. No. 4,756,427, the contents of which are herein incorporated by reference. This sorter is analogous to the sorter in the '662 patent. In this case, however, the flow in one branch is disturbed by momentarily changing the resistance of the branch. The resistance is changed by changing the height of the branch channel by an external actuator. In the preferred embodiment, this external actuator is a piezo disc glued on top of the channel, causing it to move downwards upon activation.

Although the construction of the sorter described in the '427 patent is less complex than the previously described sorter structures, it is still problematic to couple multiple sorter modules of the described type together to increase the sorting rate. This is, as in the sorter described in the '307 patent because of the generated pressure waves causing interference with other sorter modules.

Another particle sorting device is described in U.S. Pat. No. 5,837,200, the contents of which are herein incorporated by reference. The '200 patent describes a sorting device that uses a magnetic deflection module to classify or select particles based on their magnetic properties. The '200 patent further describes processing and separating individual particle streams in parallel.

SUMMARY OF THE INVENTION

The present invention provides a method and apparatus for sorting particles moving through a closed channel system of capillary size. The particle sorting system of the invention provides a sorting module that can be assembled at low cost while providing an accurate means of sorting large amounts of particles per unit of time. The particle sorting system may include a plurality of closely coupled sorting modules which are combined to further increase the sorting rate. The particle sorting system may comprise a multi-stage sorting device for serially sorting streams of particles, in order to decrease the error rate.

The particle sorting system implements an improved fluidic particle switching method and switching device according to the present invention. The particle sorting system comprises a closed channel system of capillary size for sorting particles. The channel system comprises a first supply duct for introducing a stream of particles and a second supply duct for supplying a carrier liquid. The first supply duct forms a nozzle to introduce a stream of particles into the flow of carrier liquid. The first supply duct and the second supply duct are in fluid communication with a measurement duct, which branches into a first branch and a second branch at a branch point. A measurement region is defined in the measurement duct and is associated with a detector to sense a predetermined characteristic of particles in the measurement region. Two opposed bubble valves are positioned in communication with the measurement duct and are spaced opposite each other. The bubble valves communicate with the measurement duct through a pair of opposed side passages. Liquid is allowed to partly fill these side passages to form a meniscus therein which interfaces the carrier liquid with the reservoir of the bubble valves. An external actuator is also provided for actuating one of the bubble valves. When the external actuator is activated, the pressure in the reservoir of the activated bubble valve increases, deflecting the meniscus and causing a flow disturbance in the measurement duct to deflect the flow therein.

When a sensor located in the measuring region senses a predetermined characteristic in a particle flowing through the measurement region, the sensor produces a signal in response to the sensed characteristic. The external actuator is responsive to the sensor to cause a pressure pulse in a compression chamber of a first bubble valve to deflect the particle with the predetermined characteristic, causing the selected particle to flow down the second branch duct.

In one aspect, the invention comprises a method of sorting particles including the steps of providing a measurement duct having an inlet and a branching point at which the duct separates into two branch ducts, and conducting a stream of fluid into the duct inlet with a stream of particles suspended therein, such that the particles normally flow through a first one of the branch ducts and providing upstream from the branching point two opposing side passages for momentarily deflecting the stream in the duct. A first one of the side passages is hydraulically connected to a compression chamber of a first bubble valve, which is acted upon by an external actuator for varying the pressure therein. A second of the side passages is hydraulically connected with a buffer chamber of a second bubble valve for absorbing pressure variations. The method further comprises providing a measurement station along the measurement duct upstream of the side passages for sensing a predetermined characteristic of particles in the stream and for producing a signal when the predetermined characteristic is sensed. The method further comprises the step of, in response to sensing the predetermined characteristic, activating the external actuator for creating a flow disturbance in the duct between the side passages, thereby deflecting the particle having the predetermined characteristics and causing the selected particle to flow down the second branch duct.

In further aspects of the invention, the particle sort rate is respectively increased or the type of particles sorted being increased, by respectively connecting a plurality of sorting modules in parallel or serially connecting a plurality of sorting modules in a binary tree like configuration.

According to one aspect of the invention, a particle sorting system is provided. The particles sorting system comprises a first duct for conveying a stream of suspended particles confined in a carrier liquid, comprising an inlet, a first outlet and a second outlet, a sensor for sensing a predetermined characteristic in a particle, a side channel in communication with the first duct, a sealed chamber positioned adjacent to the side channel, wherein the carrier fluid forms a meniscus in the side channel to separate the sealed chamber from the carrier fluid; and an actuator. The actuator modifies the pressure in the sealed chamber to deflect the meniscus when the sensor senses the predetermined characteristic. The deflection of the meniscus causes the particle having the predetermined characteristic to flow into the second outlet while particles that do not have the predetermined characteristic flow into the first outlet.

DETAILED DESCRIPTION OF THE INVENTION

The present invention provides a particle sorting system for sorting particles suspended in a liquid. The particle sorting system provides high-throughput, low error sorting of particles based on a predetermined characteristic. The present invention will be described below relative to illustrative embodiments. Those skilled in the art will appreciate that the present invention may be implemented in a number of different applications and embodiments and is not specifically limited in its application to the particular embodiments depicted herein.

The terms "duct" "channel" and "flow channel" as used herein refers to a pathway formed in or through a medium that allows for movement of fluids, such as liquids and gases. The channel in the microfluidic system preferably have cross-sectional dimensions in the range between about 1.0 µm and about 500 µm, preferably between about 25 µm and about 250 µm and most preferably between about 50 µm and about 150 µm. One of ordinary skill in the art will be able to determine an appropriate volume and length of the flow channel. The ranges are intended to include the above-recited values as upper or lower limits. The flow channel can have any selected shape or arrangement, examples of which include a linear or non-linear configuration and a U-shaped configuration.

The term "particle" refers to a discrete unit of matter, including, but not limited to cells.

The term "sensor" as used herein refers to a device for measuring a characteristic of an object, such as a particle.

The term "bubble valve" as used herein refers to a device that generates pressure pulses to control flow through a channel.

The term "carrier fluid" as used herein refers to a sheath of compatible liquid surrounding a particle for carrying one or more particles through a duct or channel.

Figure 1:
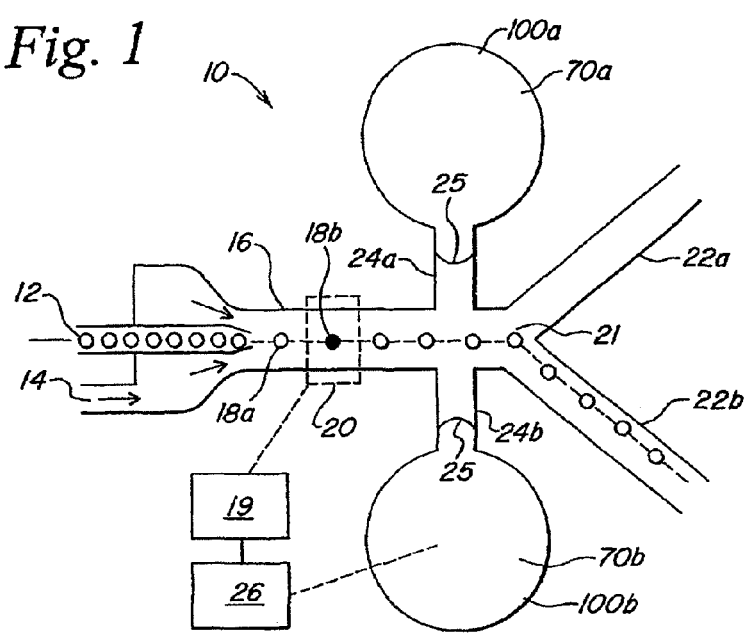
FIG. 1 is a schematic view of a particle sorting system according to an illustrative embodiment of the invention.

FIG. 1 is a schematic depiction of a particle sorting system 10 according to the teachings of the present invention. According to one application of the present invention, the particle sorting system 10 comprises a closed channel system of capillary size for sorting particles. The channel system comprises a first supply duct 12 for introducing a stream of particles 18 and a second supply duct 14 for supplying a carrier liquid. The first supply duct 12 forms a nozzle 12a, and a stream of particles is introduced into the flow of the carrier liquid. The first supply duct 12 and the second supply duct 14 are in fluid communication with a measurement duct 16 for conveying the particles suspended in the carrier liquid. The measurement duct branches into a first branch channel 22a and a second branch channel 22b at a branch point 21. A measurement region 20 is defined in the measurement duct 16 and is associated with a detector 19 to sense a predetermined characteristic of the particles passing through the measurement region 20. Two opposed bubble valves 100a and 100b are positioned relative to the measurement duct and disposed in fluid communication therewith. The valves are spaced opposite each other, although those of ordinary skill will realize that other configurations can also be used. The bubble valves 100a and 100b communicate with the measurement duct 16 through a pair of opposed side passages 24a and 24b, respectively. Liquid is allowed to partly fill these side passages 24a and 24b to form a meniscus 25 therein. The meniscus defines an interface between the carrier liquid and another fluid, such as a gas in the reservoir of the associated bubble valve 100. An actuator 26 is also provided for actuating either bubble valve, which momentarily causes a flow disturbance in the duct to deflect the flow therein when activated by the actuator 26. As illustrated, the actuator is coupled to the bubble valve 100b. The second bubble valve 100a serves as a buffer for absorbing the pressure pulse created by the first bubble valve 100b.

The first side passage 24b is hydraulically connected to a compression chamber 70b in the first bubble valve 100b, so that if the pressure in this chamber is increased, the flow in the measurement duct near the side passage is displaced inwards, substantially perpendicular to the normal flow in the duct. The second side passage 24a, positioned opposite of the first side passage 24b is hydraulically connected to a buffer chamber 70a in the second bubble valve 100a for absorbing pressure transients. This first side passage 24b co-operates with the second side passage 24a to direct the before mentioned liquid displacement caused by pressurizing the compression chamber 70b, so that the displacement has a component perpendicular to the normal flow of the particles through the measurement duct.

Upon pressurizing the compression chamber 70b an amount of liquid is transiently discharged from the first side passage 24b. The resiliency of the second side passage 24a results upon a pressurized discharge, in a transient flow of the liquid in the duct into the second side passage 24a. The co-operation of the two side passages and the fluidic structures they interconnect causes the flow through the measurement duct 16 to be transiently moved sideways back and forth upon pressurizing and depressurising of the compression chamber 70b induced by the external actuator 26 in response to the signal raised by the detection means 19. This transient liquid displacement, having a component perpendicular to the normal flow in the duct, can be applied in deflecting particles having predetermined characteristics to separate them from the remaining particles in the mixture.

As shown, the measurement duct 16 branches at the branch point 21 into two branches 22a, 22b and the flow rates in these branches are adjusted so that the particles normally stream through the second of the two branches 22b. The angle between the branches 22a, 22b is between 0 and 180 degrees, and preferably between 10 and 45 degrees. However, the angle can even be 0 degrees, which corresponds to two parallel ducts with a straight separation wall between them.

The particles to be sorted are preferably supplied to a measurement position in a central fluid current, which is surrounded by a particle free liquid sheath. The process of confining a particle stream is known, and often referred to as a 'sheath flow' configuration. Normally, confinement is achieved by injecting a stream of suspended particles through a narrow outlet nozzle into a particle free carrier liquid flowing in the duct 16. By adjusting the ratio of flow rates of the suspension and carrier liquid, the radial confinement in the duct as well as the inter particle distance can be adjusted. A relatively large flow rate of the carrier liquid results in a more confined particle stream having a large distance between the particles.

In a suspension introduced by the first supply duct 12, two types of particles can be distinguished, normal particles 18*a* and particles of interest 18*b*. Upon sensing the predetermined characteristic in a particle 18*b* in the measurement region 20, the detector 19 raises a signal. The external actuator 26 activates the first actuator bubble valve 100*b*, when signaled by the detector 19 in response to sensing the predetermined characteristic, to create a flow disturbance in the measurement duct 16 between the side passages 24*a*, 24*b*. The flow disturbance deflects the particle 18*b* having the predetermined characteristic so that it flows down the first branch duct 22*a* rather than the second branch duct 22*b*. The detector communicates with the actuator 26, so that when the detector 19 senses a predetermined characteristic in a particle, the actuator activates the first bubble valve 100*b* to cause pressure variations in the reservoir 70*b* of the first bubble valve. The activation of the first bubble valves deflects the meniscus 25*b* in the first bubble valve 100*b* and causes a transient pressure variation in the first side passage 24*b*. The second side passage 24*a* and the second bubble valve 10*a* absorb the transient pressure variations in the measurement duct 16 induced via the actuator 26. Basically, the reservoir 70*a* of the second bubble valve 10*a* is a buffer chamber having a resilient wall or containing a compressible fluid, such as a gas. The resilient properties allow the flow of liquid from the measurement duct into the second side passage 24*a*, allowing the pressure pulse to be absorbed and preventing disturbance to the flow of the non-selected particles in the stream of particles.

At the measurement region 20, individual particles are inspected, using a suitable sensor 19, for a particular characteristic, such as size, form, fluorescent intensity, as well as other characteristics obvious to one of ordinary skill. Examples of applicable sensor, known in the art, are various types of optical detection systems such as microscopes, machine vision systems and electronic means for measuring electronic properties of the particles. Particularly well known systems in the field are systems for measuring the fluorescent intensity of particles. These systems comprise a light source having a suitable wavelength for inducing fluorescence and a detection system for measuring the intensity of the induced fluorescent light. This approach is often used in combination with particles that are labelled with a fluorescent marker, i.e. an attached molecule that upon illuminating with light of a particular first wavelength produces light at another particular second wavelength (fluorescence). If this second wavelength light is detected, the characteristic is sensed and a signal is raised.

Other examples include the measurement of light scattered by particles flowing through the measurement region. Interpreting the scattering yield information on the size and form of particles, which can be adopted to raise a signal when a predetermined characteristic is detected.

The actuator 26 for pressurizing the compression chamber of the first bubble valve can comprise an external actuator that responds to a signal from the sensor that a particle has a selected predetermined characteristic. There are two classes of external actuators that are suitable for increasing the pressure. The first class directly provides a gas pressure to the liquid in the first side passage 24*b*. For example, the actuator may comprise a source of pressurized gas connected with a switching valve to the liquid column in the side passage 24*b*. Activation of the switch connects the passage to the source of pressurized gas, which deflects the meniscus in the liquid. Upon deactivation, the switch connects the passage 24*b* back to the normal operating pressure.

Alternatively, a displacement actuator may be used in combination with a closed compression chamber having a movable wall. When the displacement actuator displaces the wall of the compression chamber inward, the pressure inside increases. If the movable wall is displaced back to the original position, the pressure is reduced back to the normal operating pressure. An example of a suitable displacement actuator is an electromagnetic actuator, which causes displacement of a plunger upon energizing a coil. Another example is the use of piezoelectric material, for example in the form of a cylinder or a stack of disks, which upon the application of a voltage produces a linear displacement. Both types of actuators engage the movable wall of the compression chamber 70 to cause pressure variations therein.

Figure 2:
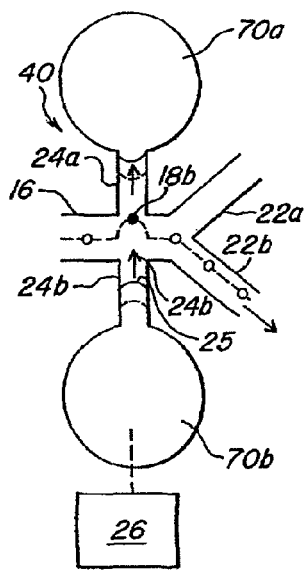
FIGS. 2 through 4 illustrate the operation of the particle sorting system of FIG. 1.
Figure 3:
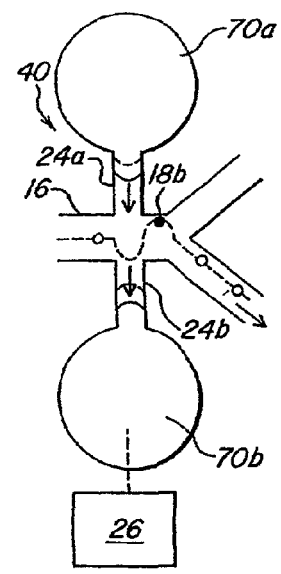
Figure 4:
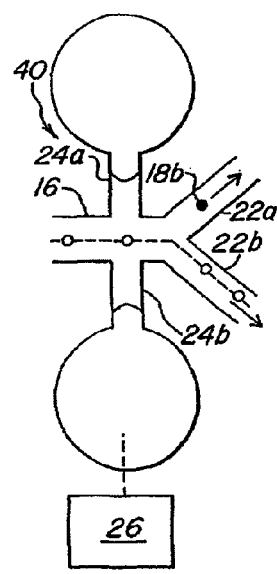

FIGS. 2 through 4 illustrate the switching operation of switch 40 in the particle sorting system 10 of FIG. 1. In FIG. 2, the detector 19 senses the predetermined characteristic in a particle and generates a signal to activate the actuator 26. Upon activation of the actuator, the pressure within the reservoir 70*b* of the first bubble valve 100*b* is increased, deflecting the meniscus 25*b* and causing a transient discharge of liquid from the first side passage 24*b*, as indicated by the arrow. The sudden pressure increase caused at this point in the duct causes liquid to flow into the second side passage 24*a*, because of the resilient properties of the reservoir of the second bubble valve 100*a*. This movement of liquid into the second side passage 24*a* is indicated with an arrow. As a result, as can be seen in the figure, the flow through the measurement duct 16 is deflected, causing the selected particle of interest 18*b* located between the first side passage 24*b* and the second side passage 24*a* to be shifted perpendicular to its flow direction in the normal state. The flow resistances to the measurement duct 16, the first branch 22*a* and the second branch 22*b* is chosen so that the preferred direction of the flow to and from the first side passage 24*b* and the second side passage 24*a* has an appreciable component perpendicular to the normal flow through the measurement duct 16. This goal can for instance be reached by the first branch 22*a* and the second branch 22*b* so that their resistances to flow is large in comparison with the flow resistances of the first side passage 24*b* and the second side passage 24*a*.

FIG. 3 shows the particle sorting system 10 during the relief of the first bubble valve reservoir when the particle of interest 18*b* has left the volume between the first side passage 24*b* and the second side passage 24*a*. The actuator 26 is deactivated, causing the pressure inside the reservoirs 70*a*, 70*b* to return to the normal pressure. During this relief phase there is a negative pressure difference between the two reservoirs 70*a*, 70*b* of the bubble valves, causing a liquid flow through the first side passage 24*b* and the second side passage 24*a* opposite to the liquid flow shown in the previous figure and as indicated by the arrows.

FIG. 4 illustrates the particle sorting system 10 after completion of the switching sequence. The pressures inside the reservoirs of the bubble valves are equalized, allowing the flow through the measurement duct 16 to normalize. As the particle of interest 18*b* has been displaced radially, it will flow into the first branch 22*a*, while the other particle continue to flow into the second branch 22*b*, thereby separating the particles based on the predetermined characteristic.

This process of detecting and selective deflecting of particles may be repeated many times per second for sorting particles at a high rate. Adopting the fluid switching as described, switching operations may be executed up to around several thousand switching operations per second, yielding sorting rates in the order of million sorted particles per hour.

Figure 5:
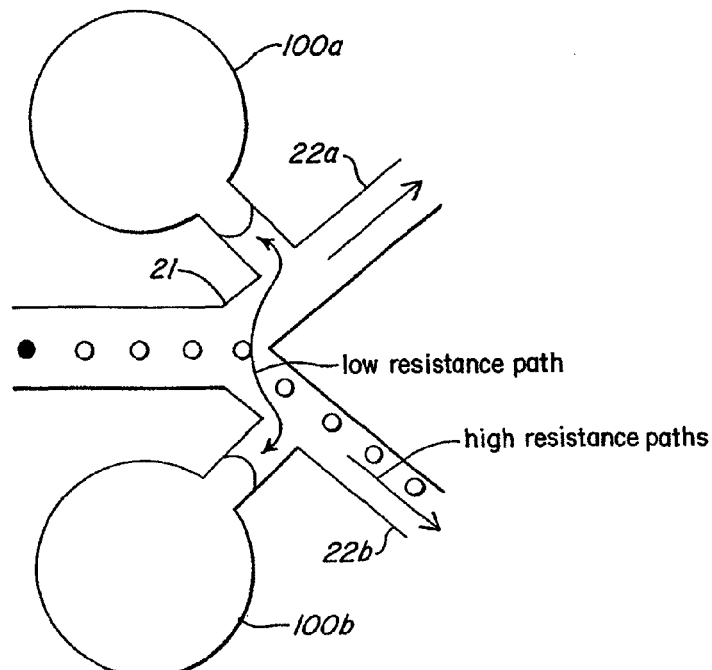
FIG. 5 illustrates a particle sorting system showing alternate positions for the actuator chamber and the buffer chamber.

According to another embodiment of the invention, the actuator bubble valve 100b and the buffer bubble valve 100a may be placed in different positions. For example, as shown in FIG. 5, the actuator bubble valve 100b and the first side passage 24b and/or the buffer bubble valve 100a and the second side passage 24a may be place upstream from the branch point 21. The components may be placed in any suitable location, such that the flow resistance between the actuator chamber 70b and the buffer chamber 70a is less than the flow resistance between any of these latter components and other pressure sources. More particularly, the actuator chamber 70b and the buffer chamber 70a may be placed such that the flow resistance between them is less than the flow resistance between a selected particle and a subsequent particle in the stream of particles. The positioning of the components in this manner thus prevents a pressure wave generated by the above-described method of deflecting a single selected particle, from travelling upstream or downstream and affecting the flow of the remaining particles in the stream of particles. A larger difference in flow resistances results in a higher level of isolation of the fluidic switching operation with associated pressure transients from the flow characteristics in the rest of the system. Moreover, the in-situ dampening of generated pressure pulses applied for sorting allows the implementation of sorting networks comprising a plurality of switches 40, each of which is hydraulically and pneumatically isolated from the others.

Figure 6:
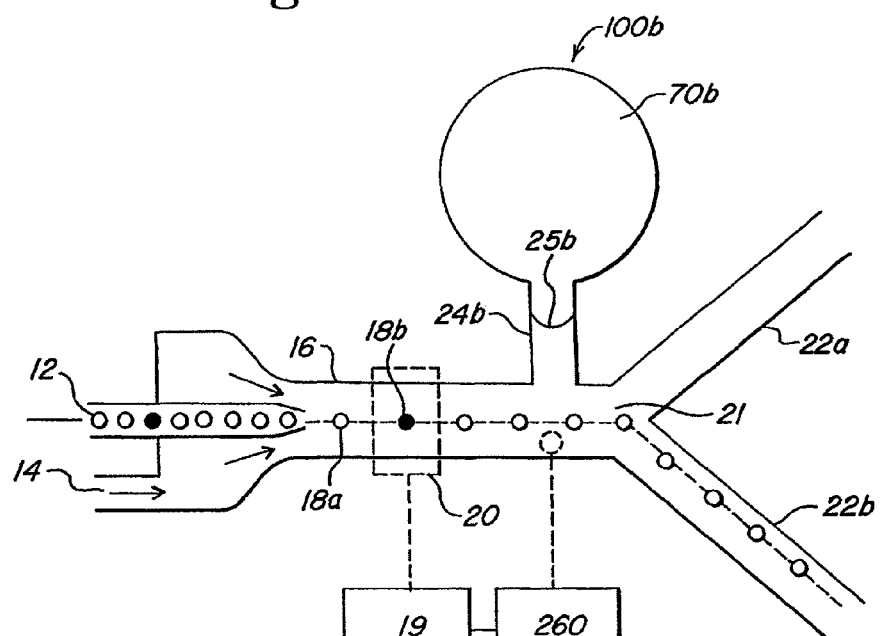
FIG. 6 illustrates the particle sorting system according to another embodiment of the invention.

According to another embodiment, shown in FIG. 6, the particle sorting system of the present invention may use any suitable pressure wave generator (in place of a bubble valve) in combination one or more bubble valves serving as a buffer, such as valve 100b. For example, the pressure wave generator 260 may comprise an actuator such as a piezoelectric column or a stepper motor, provided with a plunger that can act upon the flowing liquid, either directly or via deflection of the channel system, to selectively deflect particles when the actuator is activated by a signal. Other suitable pressure wave generators include electromagnetic actuators, thermopneumatic actuators and a heat pulse generator for generating vapor bubbles in the flowing liquid by applying heat pulses. The buffer bubble valve 100b is positioned to absorb the pressure wave created by the pressure wave generator 260 to prevent flow disturbance in the other particles of the particle stream. The spring constant of the buffer 100b may be varied according to the particular requirements by varying the volume of the buffer chamber 70b, the cross-sectional area of the side passage 24b and/or the stiffness or the thickness of a flexible membrane (reference 72 in FIG. 7) forming the buffer chamber 70b.

Figure 7:
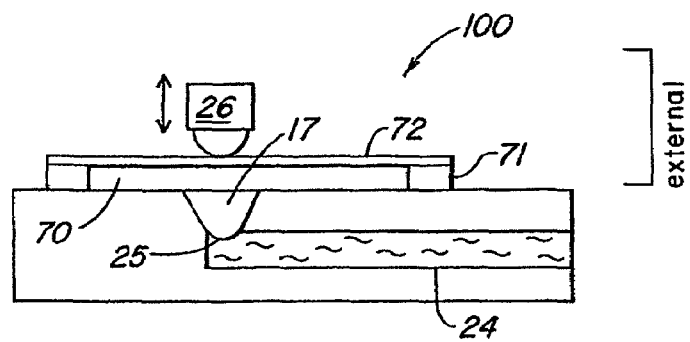
FIG. 7 illustrates a bubble valve suitable for use in the particle sorting system of the present invention.

FIG. 7 illustrates an embodiment of a valve 100 suitable for creating a pressure pulse to separate particles of interest from other particles in a stream of particles and/or acting as a buffer for absorbing a pressure pulse according to the teachings of the present invention. As shown, the valve 100 is formed adjacent to a side passage 24a or 24b formed in a substrate which leads to the measurement duct 16. The side passage 24a includes a fluid interface port 17 formed by an aperture in the side wall of the passage. A sealed compression chamber 70 is positioned adjacent to the side passage 24a and communicates with the side passage through the fluid interface port. The illustrative chamber 70 is formed by a seal 71 and a flexible membrane 72. The carrier fluid in the side passage 24a forms a meniscus 25 at the interface between the side passage and the chamber. The actuator 26 depresses the flexible membrane to increase the pressure in the chamber, which deflects the meniscus and causes a pressure pulse in the carrier fluid.

Figure 8:
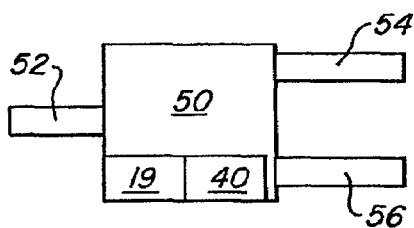
FIG. 8 is a schematic diagram of the particle sorting system of an illustrative embodiment of the present invention.

FIG. 8 shows a sorting module 50 having an appropriate supply duct 52 for providing a stream of particles to be sorted as well as a first outlet duct 54 and a second outlet duct 56, either of which can carry the particles sorted in the sorting module 50. The sorting module 50 comprises a detector system 19 for sensing particles entering the sorting module 50 via the supply duct 52 can be operationally connected to a switch 40 for providing the required switching capabilities to sort particles. The first branch 22b and the second branch 22a, FIG. 1, can be disposed in fluidic connection with the outlet duct 54 and the second outlet duct 56.

Figure 9:
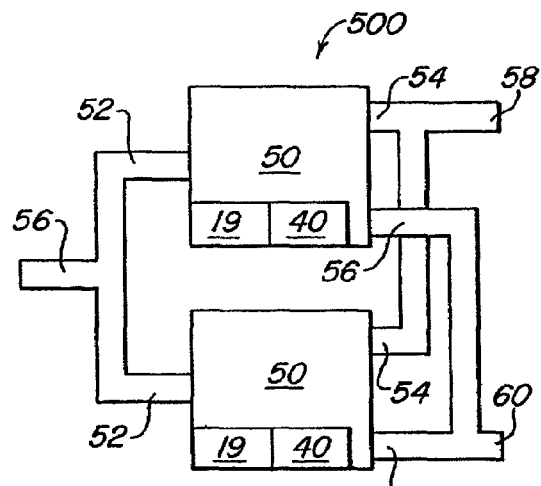
FIG. 9 shows one embodiment of a particle sorting system for sorting parallel streams of particles according to the teachings of the present invention.

FIG. 9 shows a particle sorting system 500 according to an alternate embodiment of the invention, comprising a plurality of sorting modules 50 that can be coupled together in any appropriate configuration. For example, the modules 50 in this embodiment are coupled in parallel. The outlet ducts 54 of the sorting modules 50 are coupled to a first combined outlet 58, the second outlet ducts 56 are coupled to a second combined outlet 60. The parallel arrangement of sorting modules yields a system of combined sorting module 50 having an overall sorting rate of N times the sorting rate of an individual sorting module 50, where N is the number of parallel connected sorting module 50.

Figure 10:
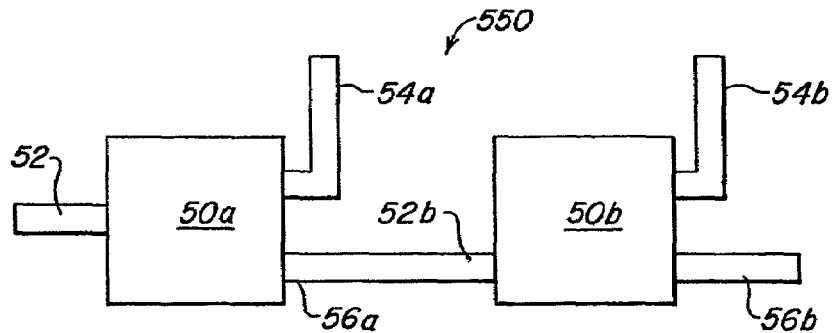
FIG. 10 shows one embodiment of a particle sorting system configured in a binary tree-like configuration of sorting modules according to the teachings of the present invention.

FIG. 10 shows a particle sorting system 550 according to another embodiment, comprising a first sorting module 50a in series with a second sorting module 50b. The second sorting module 50b may be equipped for sorting particles having a predetermined characteristic the same or different than the predetermined characteristic of the particles sorted by the first sorting module 50a. The particle stream enters the first sorting module 50a through the supply duct 52 and may contain at least two types of particles. A first type of particle is sorted in the first sorting module 50a and exits through the first outlet duct 54a. The remaining particles exit the first sorting module 50a through second outlet duct 56a and are introduced into the second sorting module 50b via the second supply duct 52b. From this stream of particles, particles having the other predetermined characteristic are sorted and exit through the second outlet duct 54b. Particles that posses neither of the two predetermined characteristics exit the second sorting module 50b via the second outlet duct 56b. Those of ordinary skill will readily recognize that any suitable type of sorting module 50 can be used, and can be coupled together in a variety of ways, depending upon the desired results.

Figure 11:
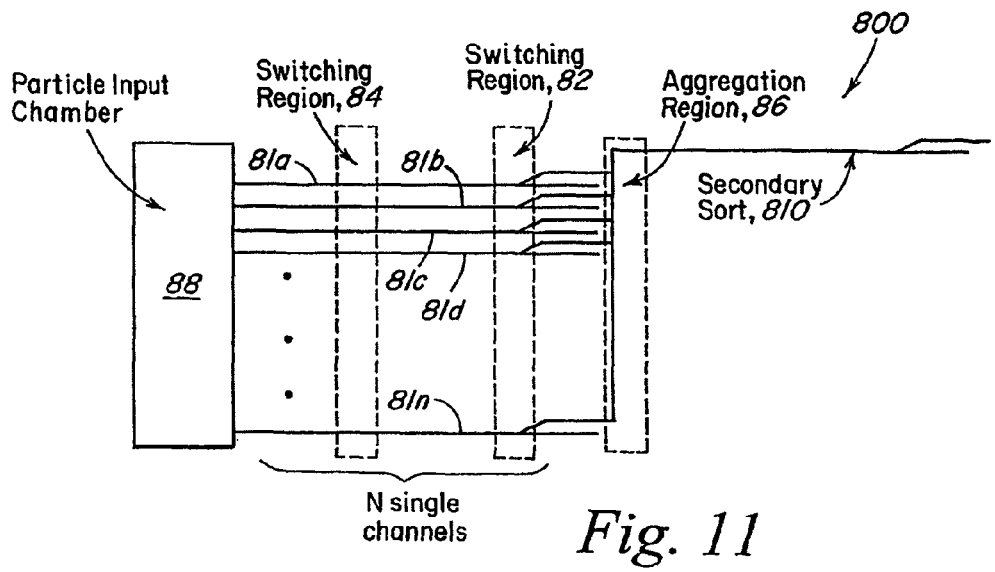
FIG. 11 illustrates another embodiment of a multi-stage particle sorting system for sorting parallel streams of particles in multiple stages.

FIG. 11 shows a hierarchical architecture for high throughput-low error sorting according to another embodiment of the present invention. The illustrated embodiment is a two-stage particle sorting system 800 for sorting a plurality of parallel particles streams in a first stage, aggregating the outputs of the first stage and then performing a secondary sorting process on the output of the first stage. An input stream of particles in suspension 80 from a particle input chamber 88 is split among N single sorting channels 81a-81n, each channel being capable of sorting a selected number of particles per second. Each channel 81 includes a detection region 84 for examining the particles and identifying particles that have a predetermined characteristic, and a switching region 82 for separating the particles having the predetermined characteristic from the other particles in the stream, as described above. The switching region 82 produces two output streams of particles: a "selected" stream and a "rejected" stream in its switching region 82 based on the measured particle characteristics at the detection region 84. The "selected" streams from each channel are aggregated in an aggregation region 86 into one stream to be sorted again in a secondary sorting channel 810. As shown, the secondary sorting channel 810 repeats the sorting process of detecting and sorting based on a predetermined characteristic.

Given that each single channel sorting process produces some error (y) rate (y is a probability less than one of a particle being "selected" by mistake) of mistaken selections, the hierarchical architecture produces an lower error rate of $y^2$ for a 2-stage hierarchy as drawn or $y^n$ for an n-stage hierarchy. For example, if the single channel error rate is 1% the 2-stage error rate is 0.01% or one part in $10^4$.

Alternatively, the architecture could have M primary sets of N sorting channels per secondary channel. Given that the application wants to capture particles that have a presence in the input at rate z and single channel sorters have a maximum sorting rate x particles per second. The system throughput is M*N*x in particles per second. The number of particles aggregated in N channels per second is N*x*z and so N*z must be less than 1 so that all particles aggregated from N channels can be sorted by a single secondary channel. To increase throughput above N=1/z one must add parallel groups of N primary+1 secondary channels. Overall throughput then comes from M*N*x with M secondary channels.

Figure 12:
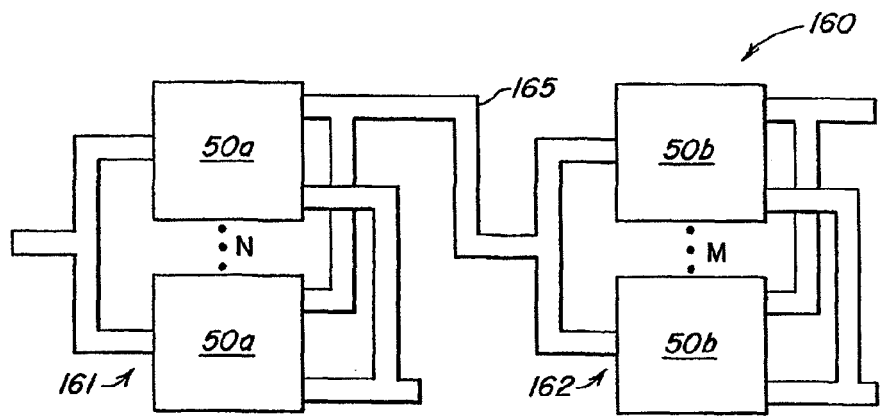
FIG. 12 illustrates a parallel particle sorting system according to an alternate embodiment of the present invention.

FIG. 12 show a parallel-serial particle sorting system 160 according to another embodiment of the invention. The parallel-serial particle sorting system 160 includes a first parallel sorting module 161 and a second parallel sorting module 162. The first sorting module 161 is applied in multiple marked particles and particles having both markers are sorted out and conveyed through the exit channel 165.

Figure 13:
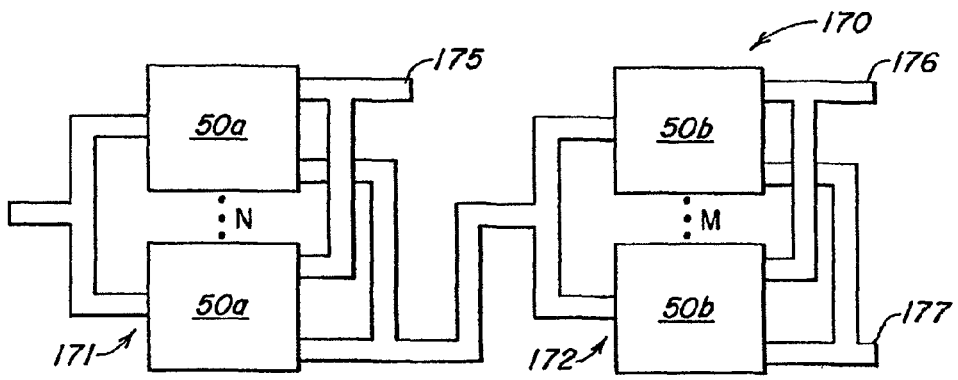
FIG. 13 illustrates a parallel particle sorting system according to another embodiment of the present invention.

FIG. 13 shows another parallel-serial particle sorting system 170. The first parallel sorting module 171 separates particles having a first marker, collects the particles from the different channels and conveys the particles having the first marker through the first exit channel 175. All other particles are then fed into a second parallel sorter 172 for sorting particles having a second marker. The particles having the second marker are collected and conveyed through a second exit channel 176. Particles having neither the first marker nor the second marker are conveyed through a third exit channel 177.

Figure 14A:
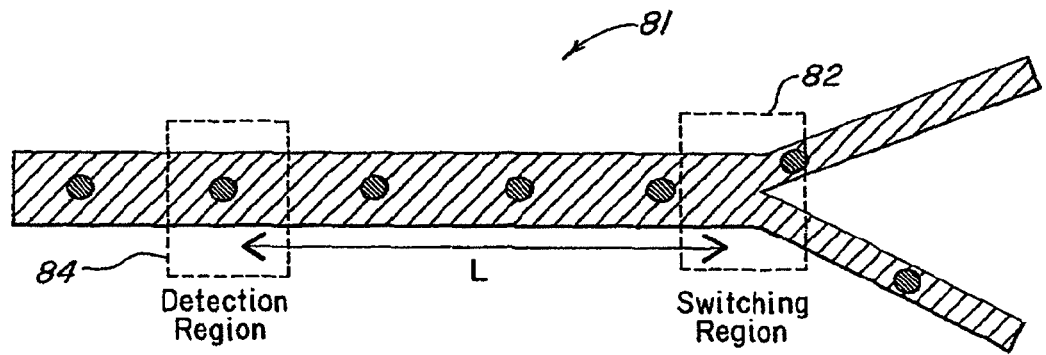
FIGS. 14a and 14b illustrate a particle sorting system according to another embodiment of the invention, including an optical mask to allow measurement of a particle size and/or velocity.
Figure 14B:
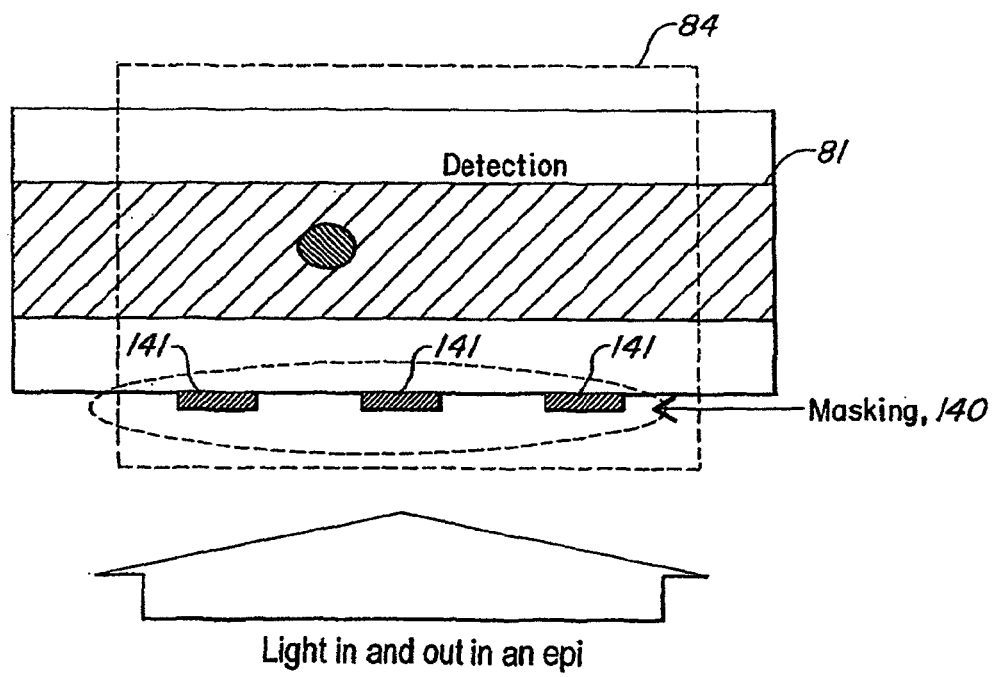

According to one embodiment of the invention, shown in FIGS. 14a and 14b, the particle sorting system may include sensors for measuring velocity, location and/or size of particles. The measurement of velocity, location and/or size may be made simultaneously with classification of the particles for sorting or at a different time. In parallel channel based systems, as shown in FIG. 11, the different channels may have different flow resistances, causing the velocity of the particles or cells in each channel to be different. In systems where the detection region 84 is separated from the switching region 82 by a distance L, the velocity of the particles in the channel 81 must be known in order to set the switching time delay T (i.e., the time to delay switch actuation relative to the moment of detection of a target particle).

In most optical systems for detecting cells or particles, the region in which the cell creates light on the photo detector in the detection region will have a much greater size than the size of a cell diameter. Therefore, when light is detected in the detection region, the cell may be anywhere in the region, making it difficult to pinpoint the exact location of the cell. To provide more accurate detection, many pixels of an optical detector could be packed across the detection region, but this would have a large cost and require complex support electronics.

According to an illustrative embodiment of the invention, an optical mask 140 may be added to the detection region to provide accurate velocity detection by depositing a "masking pattern" directly on the sorting chip. The masking patterns can be deposited so that an edge in the masking pattern is precisely located (to <1 um precision with current technology) relative to the cell sorting actuator region 82. A single optical detector catching light from the cell in the detection region 84 will see light when the cell is not masked. The duration of the light being turned off by one of the connected opaque parts "bars" of the mask of known length gives a measurement of velocity.

A mask pattern that has several bars 141 of size ranging from 10 um to 30 um in 1 um steps results in only bars of size larger than the cell minimizing the signal from the cell. Therefore, such a pattern can also be used to measure the size of the cell independently of its signal. Such a "gradient mask" also produces a pattern in the optical detector that can be analyzed to measure velocity several times for reducing the variance in the velocity estimate. The pattern in the light induced by the mask 140 also allows the detector to identify each edge in the mask 140. If the bars 141 were all the same, the light signal for each bar would be the same, and one could only tell them apart by sequence. Therefore, a gradient mask pattern will allow a single detector looking at a broad region (several times the size of a cell) to measure the velocity of the cell, measure the exact position inside the detection region 84 with about 1 um precision relative to the channel structures and the actuator location on chip and identify the size of the cell to precision given by the gradient pattern. The gradient mask 140 allows the detector to measure these parameters independent of the magnification of the optical system or the nature of the optical detector itself.

One skilled in the art will recognize that other devices for measuring the size, position and or velocity of a particle in the sorting system in accordance with the teachings of the invention. Suitable devices are readily available and known to those of ordinary skill in the art.

Figure 15:
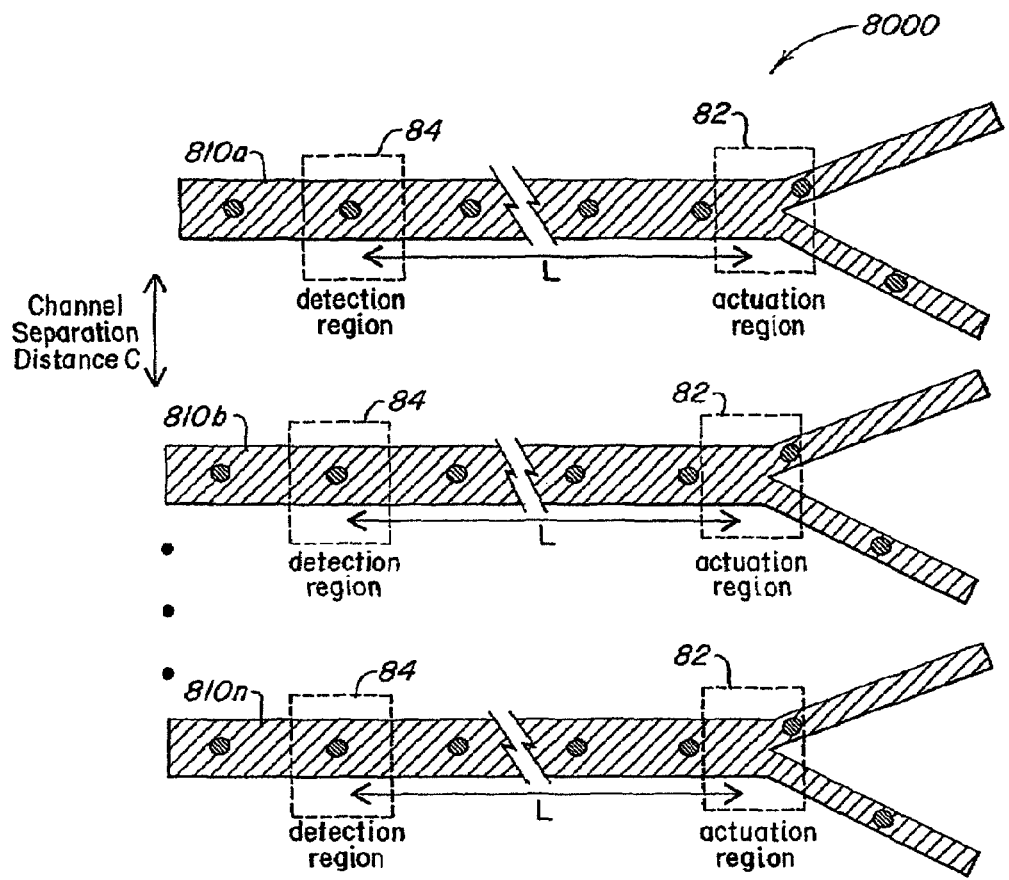
FIG. 15 illustrates a parallel sorting system having variable channels according to another embodiment of the present invention.

According to another embodiment, shown in FIG. 15, the particle sorting system comprises an array 8000 of non-identical sorting channels. The use of a parallel array comprising a series of non-identical sorter channels 810a-810n is more efficient in terms of space, use of optical power and adaptation to optimal external actuators. Since the velocity of particles can be accurately sensed using a sensor as described above, the channels do not require a fixed delay between the detection of a property and actuation of a switch to deflect a particle having the detected property. Therefore, certain parameters of the channel, such as the distance L between a detector 84 and a switch 82 or the shape of the path between the detector 84 and the switch 82 can be varied.

Using a single laser for each wavelength optical illumination directed perpendicular to the chip, the laser is required to illuminate an area defined by: (number of channels)×((channel width at detection region)+(inter channel spacing C)) (See FIG. 15). However, the active area where light can be absorbed to create fluorescence is only the area of the channels: (number of channels)×(channel width), which leaves a fill factor of: (channel width)/(channel width+C). The fill factor is preferably close to 100% to avoid wasting available input light.

Figure 16:
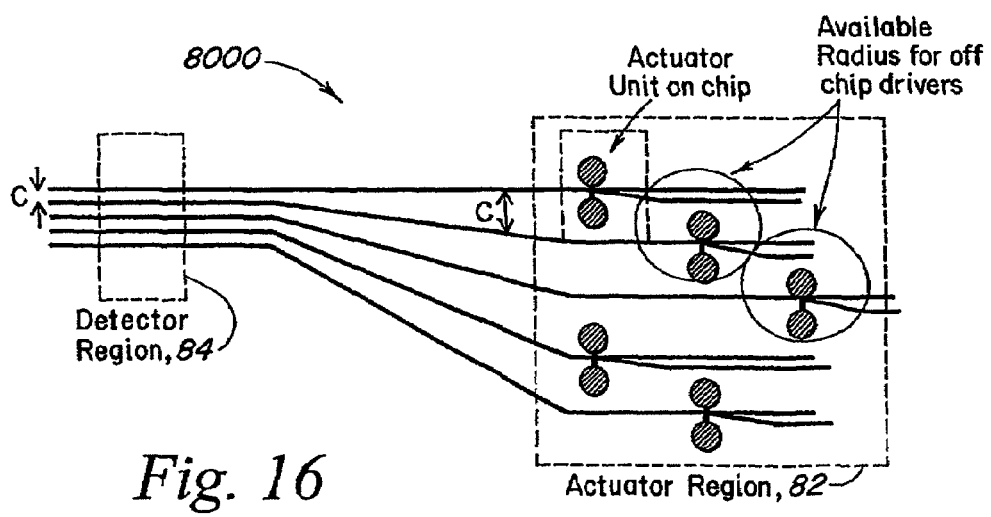
FIG. 16 illustrates a variable array design of a parallel sorting system according to another embodiment of the present invention.

Therefore, minimizing the interchannel spacing in a parallel sorting system is important to the optical detection region and optical system efficiency. In the variable array design of the present invention, shown in FIG. 16, the spacing of the channels in the detection region 84 approaches the width of the channels, so that light utilization approaches about 50%. The channel spacing in the actuation region 82 may be larger, as shown in FIG. 16. The location of actuators 26 along the channel may also be varied to make a larger available radius for external driver actuators.

The variable array 8000 may also include meanders in selected channels for balancing flow resistances of all the channels so that given a constant pressure drop across all the channels the velocities of particles are nearly matched. These can be added either upstream or downstream of the illustrated system, i.e., on in the region between the detectors and actuators. As the lengths Li between each channel's detection region 82I and its actuator 26i is known from the design, the measurement of the particle velocity at the same time as the determination regarding which particles to keep provides an improved cell sorting system.

Figure 17:
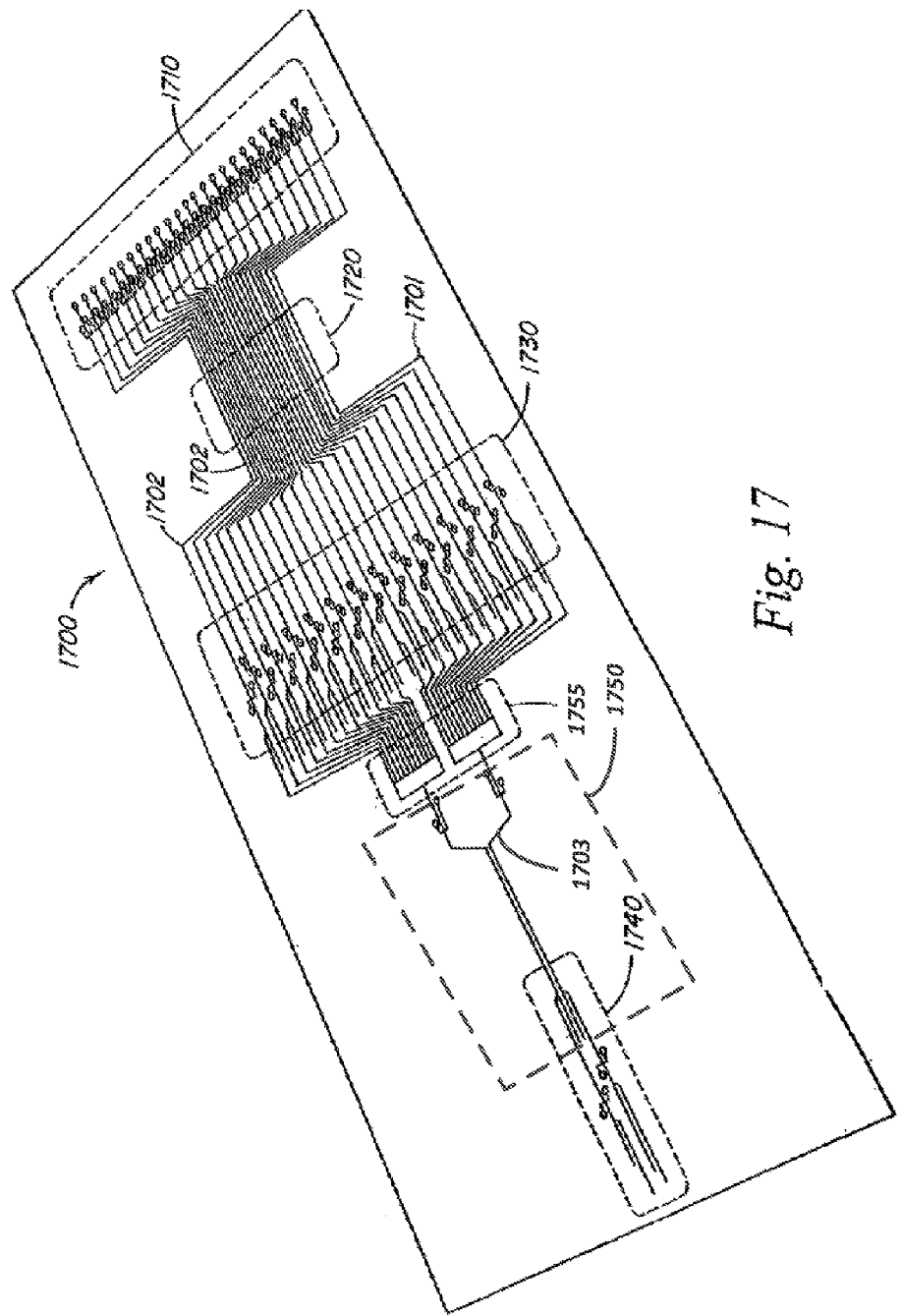
FIG. 17 illustrates a parallel sorting system according to another embodiment of the present invention.

FIG. 17 illustrates a particle sorting system 1700 according to yet another embodiment of the invention. The particle sorting system 1700 includes a plurality of sorting modules 1701 operating in parallel. The system 1700 includes an input region 1710 for introducing samples to each sorting module and a detection region 1720 for measuring a predetermined characteristic of particles each sorting channel 1702 in the detection region. The system also includes a switch region 1730, including an actuator in each sorting module for separating particles having a predetermined characteristic from particles that do not have the predetermined characteristic. As shown, in the embodiment of FIG. 17, the sorting channels 1702 distance between each sorting channel in the detection region 1720 is less than the inter-channel distance in the switch region 1730. The close spacing in the detection region enables cost saving when a laser is used to detect the particles, while the more distant separation in the switch region 1730 accommodates various sized actuators.

The particle sorting system 1700 may also include a secondary sorting module 1740 for repeating the sorting process of detecting and sorting based on a predetermined characteristic to increase the accuracy of the sorting process. According to one embodiment, the system may include an aggregation region 1755 between the array of primary sorting modules 1701 and the secondary sorting module 1740 for combining outputs from the array of primary sorting modules 1701 into one or more outlet channels, e.g., outlet channel 1703. In further embodiments, the system may include an enrichment region 1750 between the array of primary sorting modules 1701 and the secondary sorting module 1740 for transitioning the particles from the primary sorting process to the secondary sorting process. According to an illustrative embodiment such as depicted in FIG. 18, the enrichment region 1750 transitions the particles by removing excess carrier fluid from the particles before passing the particles to the secondary sorting module 1740.

Figure 18:
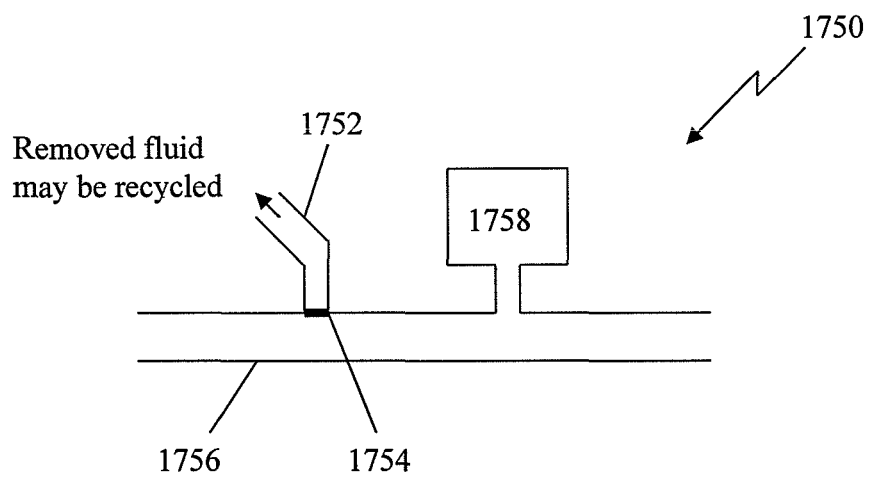
FIG. 18 illustrates an enrichment region according to various embodiments of the present invention.

As depicted in FIG. 18, the enrichment region 1750 may comprise a membrane 1754 inserted into a channel 1756, e.g., an outlet channel such as outlet channel 1703 of FIG. 17 or an output channel such as an output channel from one of the array of primary sorting modules 1701 of FIGS. 17, and an enrichment channel 1752 intersecting the channel 1756, wherein the membrane 1754 separates the channel 1756 from the enrichment channel 1752, as depicted in FIG. 20. Excess carrier fluid is removed from the stream of selected particles in the channel 1756 through the membrane 1754 and into the enrichment channel 1752 before passing the selected particles into a secondary sorting module, e.g., the secondary sorting module 1740. The enrichment region 1750 may also include a hydration device 1758 for adding secondary sheath fluid to the particles after enrichment.

A suitable system for forming the enrichment region is described in U.S. Pat. No. 6,878,271 to Gilbert et al., filed on even date herewith, the contents of which are herein incorporated by reference.

According to an exemplary embodiment, removed carrier fluid may be recycled and fed back into the inlet of primary channels. Thus, a recycling channel or other device may connect the enrichment region, e.g., the enrichment region 1750 of FIG. 18 to a primary channel, e.g., the sorting channels 81a-81n of FIG. 11, to allow re-use of the carrier fluid for subsequent sorting process. Alternatively, carrier fluid may be removed from rejected particles and introduced into the primary channel inlets prior to discarding the rejected particles. The enrichment channel 1752 of FIG. 18 may serve as a recycling channel.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A particle sorting system, comprising:
   a plurality of primary sorting channels each of which is adapted to receive a stream of suspended particles confined in a carrier liquid, wherein each of the primary sorting channels extends through one of one or more detection regions adapted for detecting one or more predetermined characteristics in a particle, wherein at least one of the detection regions comprises one or more sensors for measuring a velocity of a particle in a primary sorting channel, and wherein each of the primary sorting channels includes a switching region adapted for separating particles into first and second receiving channels based on the one or more predetermined particle characteristics;
   an aggregation chamber downstream of the switching regions adapted for aggregating the particles from at least three of the first receiving channels corresponding to at least three of the switching regions into one or more outlet channels;
   an enrichment region downstream of the aggregation chamber adapted for adjusting a volume of carrier liquid; and
   at least one secondary sorting channel in series with the plurality of parallel primary sorting channels and downstream of the enrichment region, the at least one secondary sorting channel adapted for receiving particles from one of the outlet channels and for separating the particles received from the one of the outlet channels based on the same one or more predetermined particle characteristics as used in the switching regions corresponding to the primary sorting channels.

2. The system of claim 1, wherein the enrichment region is adapted for removing excess carrier liquid.

3. The system of claim 1, wherein the enrichment region comprises:
   an enrichment channel intersecting one of said receiving channels; and a membrane separating the enrichment channel from said receiving channel.

4. The system of claim 1, wherein the enrichment region comprises:
   an enrichment channel intersecting said aggregation chamber; and
   a membrane separating the enrichment channel from the aggregation chamber.

5. The system of claim 1, wherein the enrichment region comprises:
   an enrichment channel intersecting one of said outlet channels; and
   a membrane separating the enrichment channel from said outlet channel.

6. The system of claim 2, further comprising a hydration device for adding secondary carrier fluid to the particles after the enrichment region.

7. The system of claim 2, further comprising a recycling channel connecting the enrichment region to the primary sorting channel for introducing the removed excess carrier liquid into the primary sorting channel.

8. A method of sorting particles, comprising:
   conveying a plurality of streams of suspended particles confined in a carrier liquid through a plurality of parallel primary sorting channels, wherein each of the primary sorting channels extends through one of one or more detection regions adapted for detecting one or more predetermined characteristics in a particle, wherein at least one of the detection regions comprises one or more sensors for measuring a velocity of a particle in a primary sorting channel, and wherein each of the primary sorting channels includes a switching region adapted for separating particles into first and second receiving channels based on the one or more predetermined particle characteristics;
   separating particles into the first and second receiving channels based on the one or more predetermined particle characteristics;
   aggregating the particles from at least three of the first receiving channels corresponding to at least three of the switching regions into one or more outlet channels in an aggregation chamber downstream of the switching regions;
   adjusting a volume of carrier liquid in an enrichment region downstream of the aggregation chamber;
   conveying particles from one of the outlet channels through at least one secondary sorting channel in series with the plurality of parallel primary sorting channels and downstream of the enrichment region; and
   separating the particles in the at least one secondary sorting channel based on the same one or more predetermined particle characteristics as used in the switching regions corresponding to the primary sorting channels.

9. The system of claim 1, wherein each of the primary switching regions is adapted to sort selected particles substantially all of which have the one or more predetermined particle characteristics into the first receiving channel and all other particles into the second receiving channel and wherein the secondary sorting channel is adapted to further sort the selected particles.

10. The system of claim 9, wherein the enrichment region is adapted for adjusting a volume of carrier liquid around the selected particles.

11. The system of claim 1, wherein the enrichment region is adapted for adjusting a volume of carrier liquid around aggregated particles from the aggregation chamber.

12. The system of claim 1, wherein the number of secondary sorting channels is fewer than the number of primary sorting channels.

13. A particle sorting system, comprising:
   a plurality of primary sorting channels each of which is adapted to receive a stream of suspended particles confined in a carrier liquid, wherein each of the primary sorting channels extends through one of one or more detection regions adapted for detecting one or more predetermined characteristics in a particle, wherein at least one of the detection regions comprises one or more sensors for measuring a velocity of a particle in a primary sorting channel, and wherein each of the primary sorting channels includes a switching region adapted for separating particles into first and second receiving channels based on the one or more predetermined particle characteristics;
   an aggregation chamber downstream of the switching regions adapted for aggregating the particles from each of the first receiving channels;
   an enrichment region downstream of the aggregation chamber adapted for adjusting a volume of carrier liquid; and
   a plurality of secondary sorting channels in series with the plurality of parallel primary sorting channels and downstream of the enrichment region, the plurality of secondary sorting channels adapted for receiving the aggregated particles from the aggregation chamber and for separating the received particles based on the same one or more predetermined particle characteristics as used in the switching regions corresponding to the primary sorting channels.

* * * * *